US 6,695,779 B2

(12) United States Patent
Sauer et al.

(10) Patent No.: US 6,695,779 B2
(45) Date of Patent: Feb. 24, 2004

(54) METHOD AND APPARATUS FOR SPATIOTEMPORAL FREEZING OF ULTRASOUND IMAGES IN AUGMENTED REALITY VISUALIZATION

(75) Inventors: Frank Sauer, Princeton, NJ (US); Ali Khamene, Plainsboro, NJ (US); Benedicte Bascle, Plainsboro, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 10/222,333

(22) Filed: Aug. 16, 2002

(65) Prior Publication Data

US 2003/0060706 A1 Mar. 27, 2003

Related U.S. Application Data

(60) Provisional application No. 60/312,872, filed on Aug. 16, 2001, provisional application No. 60/312,876, filed on Aug. 16, 2001, provisional application No. 60/312,871, filed on Aug. 16, 2001, provisional application No. 60/312,875, filed on Aug. 16, 2001, and provisional application No. 60/312,873, filed on Aug. 16, 2001.

(51) Int. Cl.$^7$ ................................................ A61B 8/00
(52) U.S. Cl. ...................................................... 600/437
(58) Field of Search ................................ 600/407–471; 367/7, 11, 130, 138; 73/595–630; 128/916

(56) References Cited

U.S. PATENT DOCUMENTS 5,795,297 A * 8/1998 Daigle ......................... 600/447
6,503,195 B1 * 1/2003 Keller et al. ................. 600/160

* cited by examiner

Primary Examiner—Ali M. Imam

(57) ABSTRACT

A method for visualization of ultrasound images comprises the steps of deriving ultrasound images of an object; freezing and storing in space and time selected ones of the images; displaying the selected ones of the images as a set; selectively freezing and adding to the set a further one of the images; and, optionally, selectively removing an image from the set.

16 Claims, 1 Drawing Sheet

Figure 1:
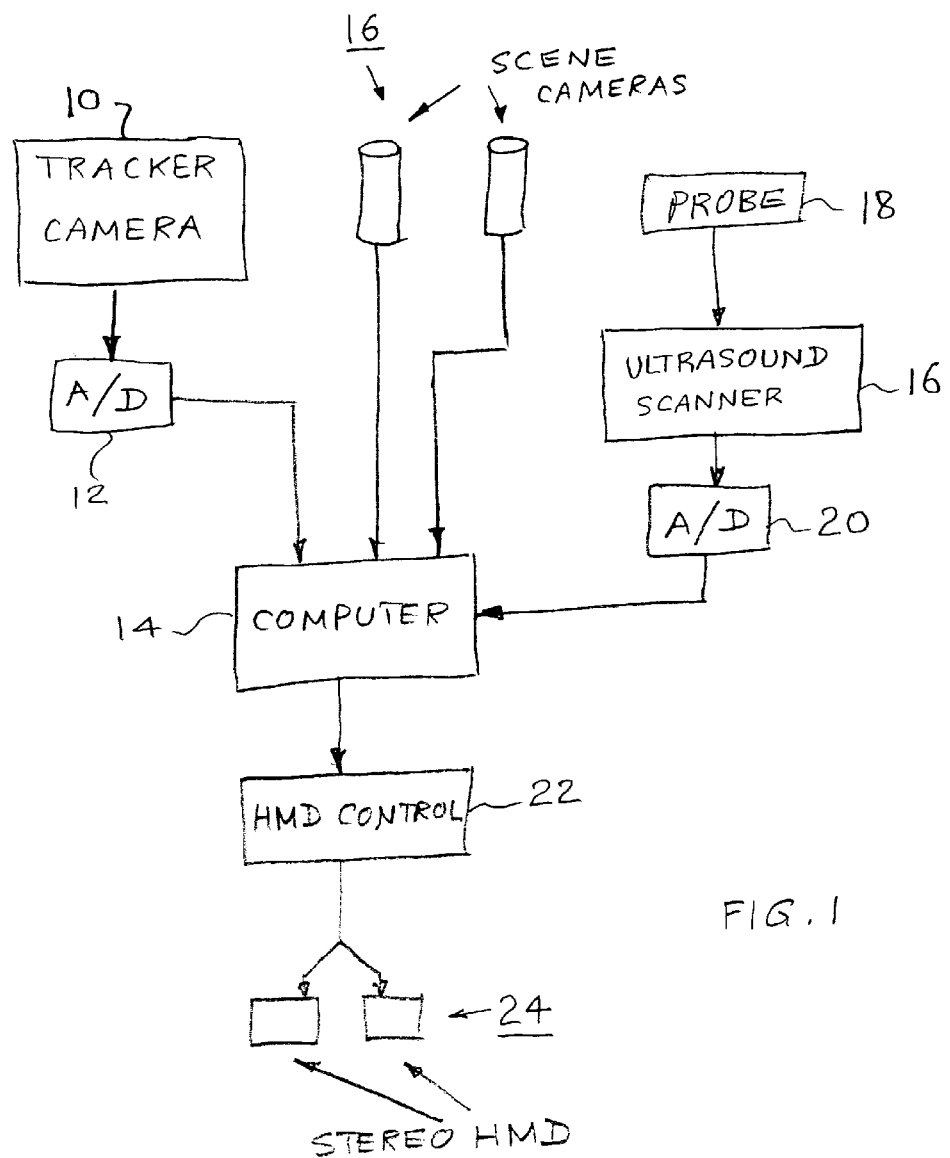

METHOD AND APPARATUS FOR SPATIOTEMPORAL FREEZING OF ULTRASOUND IMAGES IN AUGMENTED REALITY VISUALIZATION

Reference is hereby made to the following U.S. Provisional patent applications whereof the benefit is hereby claimed and whereof the disclosures are hereby incorporated by reference:

U.S. Provisional patent application No. 60/312,872, entitled MARKING 3D LOCATIONS FROM ULTRASOUND IMAGES and filed Aug. 16, 2001 in the names of Frank Sauer, Ali Khamene, Benedicte Bascle;

U.S. Provisional patent application No. 60/312,876, entitled LOCAL 3D RECONSTRUCTION FROM ULTRASOUND IMAGES and filed Aug. 16, 2001 in the names of Frank Sauer, Ali Khamene, Benedicte Bascle;

U.S. Provisional patent application No. 60/312,871, entitled SPATIOTEMPORAL FREEZING OF ULTRASOUND IMAGES IN AUGMENTED REALITY VISUALIZATION and filed Aug. 16, 2001 in the names of Frank Sauer, Ali Khamene, Benedicte Bascle;

U.S. Provisional patent application No. 60/312,875, entitled USER INTERFACE FOR AUGMENTED AND VIRTUAL REALITY SYSTEMS and filed Aug. 16, 2001 in the names of Frank Sauer, Lars Schimmang, Ali Khamene; and U.S. Provisional patent application No. 60/312,873, entitled VIDEO-ASSISTANCE FOR ULTRASOUND GUIDED NEEDLE BIOPSY and filed Aug. 16, 2001 in the names of Frank Sauer and Ali Khamene.

Reference is hereby made to the following copending U.S. patent applications being filed on even date herewith.

U.S. patent application, entitled MARKING 3D LOCATIONS FROM ULTRASOUND IMAGES filed in the names of Frank Sauer, Ali Khamene, Benedicte Bascle;

U.S. patent application entitled LOCAL 3D RECONSTRUCTION FROM ULTRASOUND IMAGES and filed in the names of Frank Sauer, Ali Khamene, Benedicte Bascle;

U.S. patent application entitled USER INTERFACE FOR AUGMENTED AND VIRTUAL REALITY SYSTEMS and filed in the names of Frank Sauer, Lars Schimmang, Ali Khamene; and U.S. patent application entitled VIDEO-ASSISTANCE FOR ULTRASOUND GUIDED NEEDLE BIOPSY and filed in the names of Frank Sauer and Ali Khamene.

The present invention relates to the field of ultrasound imaging and, more particularly, to augmented reality visualization of ultrasound images and to the freezing of ultrasound images both in time and in space.

Ultrasound scanners capture live 2D images from within objects or patients. Typically, scanners have a standard option to freeze an image in time and display the still image on the screen for evaluation, such as for example, for measuring spatial dimensions in the image.

Augmented Reality visualization of ultrasound images means that the ultrasound images are displayed as an overlay onto a view of the real object that is being scanned. The overlay is performed in a way such that the ultrasound images appear in the actual scan plane. Structures seen in the ultrasound image are registered to the corresponding real structures and appear in the actual spatial location of these physical structures. Preferably, the AR visualization is stereoscopic to give the user 3D perception.

FIG. 1 show a schematic block diagram of an augmented reality system as may be utilized in conjunction with features of the invention. A tracker camera 10 is coupled by way of and A/D (analog to digital) converter 12 to a programmable digital computer 14. Two scene cameras 16 are coupled to computer 14. An ultrasound scanner 16, having a transducer 18, is coupled by way of an A/D converter 20 to computer 14. A head-mounted display (HMD) control unit 22 is coupled for signal interchange with computer 14 and to an HMD display 24.

Augmented Reality visualization of ultrasound images has been proposed in the literature; see for exampled, M. Bajura, H. Fuchs, and R. Ohbuchi. "Merging Virtual Objects with the Real World: Seeing Ultrasound Imagery within the Patient." Proceedings of SIGGRAPH '92 (Chicago, Il., Jul. 26–31, 1992). In Computer Graphics 26, #2 (July 1992): 20

Ultrasound scanners are commonly utilized to capture live 2D images from within objects or patients. Scanners typically have a standard option to freeze an image in time and display the still image on the screen for evaluation, e.g. for measuring spatial dimensions in the image.

Helpful background material on augmented reality and related topics can be found in Proceedings of the IEEE and ACM International Symposium on Augmented Reality 2000, dated Oct. 5–6, 2000; Munich, Germany; IEEE Computer Society, Los Alamitos, Calif., U.S.A. In the above-cited Proceedings, an article of particular interest entitled AUGMENTED WORKSPACE: DESIGNING AN AR TESTBED is published on pages 47–53, and is authored by Frank Sauer, an inventor in the present application, et alii.

See also the review article by R. T. Azuma: "A Survey of Augmented Reality", Presence: Teleoperators and Virtula Environments, 6(4), 355–386, (1997).

It has also been proposed to build up 3D volume information from a set of ultrasound images. In conjunction with augmented reality visualization, it has been proposed and demonstrated not to only show the current ultrasound image in the augmented view, but to let each ultrasound image stay (at its correct location) for a while, letting it fade away over a defined time period. As long as the ultrasound transducer is being moved, there would always be a set of different ultrasound images that are being displayed simultaneously. This method is helpful to provide the user with some kind of 3D perception of the scanned volume, but it requires the user to keep moving the transducer so as not to lose the image of the structures of interest.

It is herein recognized that, at least in principle, one might keep all the ultrasound images, building up a permanent 3D ultrasound image. However, this is recognized to be computationally very demanding and, furthermore, it is likely to be confusing to the user, with the display of too many structures.

In accordance with an aspect of the present invention, selected ultrasound images are made stay in the augmented image on a trigger signal, and are made disappear on a trigger signal.

The invention will be more fully understood from the following detailed description of a preferred embodiment in accordance with the best mode of practicing the invention, in conjunction with the Drawing, in which FIG. 1 shows a block diagram of an augmented reality system.

In order to practice a preferred embodiment in accordance with the principles of the present invention in an operational set-up, the following will typically be required. An ultrasound scanner and a tracking arrangement is needed to track the ultrasound transducer. In augmented reality (AR) applications, tracking means to track from the user's viewpoint. A calibration procedure is needed and a computer for generating graphics. For AR applications, a computer is utilized for overlaying computer images onto video frames. User interface items, such as a footswitch, speech interfacing, will also include extra buttons on the transducer for the present functions. For convenience, the trigger signal is a signal from the user, who selects a particular ultrasound image of interest and freezes it in space (and time). Also, the trigger signal to deselect a particular image is preferably a user input.

Optionally, a user may delete the latest image with or without selecting another ultrasound image to be frozen and optionally, also may just add a new frozen image to the existing list.

A practical implementation reserves memory space for a maximum number of ultrasound images to be stored and displayed simultaneously. When the user selects new images to be frozen beyond the maximum number, he is required to choose which of the previous images on the list he wants to be deleted and replaced. A simple choice would be to replace either the oldest or the latest of the images in the current list. Such a choice may optionally be performed automatically in accordance with the principles of the present invention.

Furthermore, in accordance with the present invention, selected images may be retained frozen in space and time in preference to others. The possibility of freezing selected ultrasound images in space and time facilitates the user's perception of the internal structures that are being scanned.

The present invention also facilitates purely virtual reality viewing of a set of ultrasound slices. This needs tracking of the transducer relative to a stationary coordinate system, but does not require registration with a real image of the scanned object.

While the invention has been explained by way of exemplary embodiments, it will be understood by one of skill in the art to which it pertains that various modifications and changes may be readily made without departing from the spirit of the invention which is defined by the claims following.

What is claimed is:

1. A method for visualization of ultrasound images, comprising the steps of:

deriving ultrasound images of an object maintained in a stationary position;

freezing selected ones of said images;

storing the frozen selected ones of said images and a spatial position of a transducer at a time corresponding to when each frozen image was derived, the spatial position of the transducer being relative to a stationary coordinate system associated with the object being scanned;

displaying said selected ones of said images as a set in a spatial configuration where each selected image is spatially arranged according to the spatial position in which the selected image was frozen relative to the stationary coordinate system associated with the object; and selectively freezing and adding to said set a further one of said images.

2. A method for visualization of ultrasound images as recited in claim 1, wherein said steps of selectively freezing and selectively removing are performed under operator control.

3. A method for visualization of ultrasound images as recited in claim 1, wherein a step of selectively removing is automatically performed upon a predetermined number of images in said set being reached.

4. A method for visualization of ultrasound images, comprising the steps of:

deriving tracking information for a transducer utilized for deriving said ultrasound images;

deriving and storing tracking information for an operator's viewpoint;

deriving ultrasound images of an object maintained in a stationary position;

freezing selected ones of said images;

storing the frozen selected ones of said images and tracking information for the transducer corresponding to a spatial position of the transducer at a time when each frozen image was derived, the spatial position of the transducer being relative to a stationary coordinate system associated with the object being scanned; and displaying said selected ones of said images as a set utilizing said tracking information for said transducer and for said operator's viewpoint such that the set of images is displayed in a spatial configuration where each selected image is spatially arranged according to the spatial position in which the selected image was frozen relative to the stationary coordinate system associated with the object; and selectively freezing and adding to said set a further one of said images.

5. A method for visualization of ultrasound images as recited in claim 4, wherein said step of selectively freezing is performed by said operator.

6. A method for visualization of ultrasound images as recited in claim 4, wherein a step of selectively removing is automatically performed upon a predetermined number of images in said set being reached.

7. Apparatus for augmented reality visualization of ultrasound images, comprising:

means for deriving ultrasound images of an object maintained in a stationary position;

means for freezing selected ones of said images;

means for storing the frozen selected ones of said images and a spatial position of a transducer at a time corresponding to when each frozen image was derived, the spatial position of the transducer being relative to a stationary coordinate system associated with the object being scanned;

means for displaying said selected ones of said images as a set in a spatial configuration where each selected image is spatially arranged according to the spatial position in which the selected image was frozen relative to the stationary coordinate system associated with the object;

means for selectively freezing and adding to said set a further one of said images; and means for selectively removing an image from said set.

8. Apparatus for augmented reality visualization as recited in claim 7, including means for performing said steps of selectively freezing and selectively removing under operator control.

9. Apparatus for augmented reality visualization as recited in claim 7, including means for selectively removing upon a predetermined number of images in said set being reached.

10. Apparatus for augmented reality visualization of ultrasound images, comprising:

means for deriving tracking information for a transducer utilized for deriving said ultrasound images;

means for deriving and storing tracking information for video generated from an operator's viewpoint;

means for deriving ultrasound images of an object maintained in a stationary position;

means for freezing selected ones of said images;

means for storing the frozen selected ones of said images and tracking information for the transducer corresponding to a spatial position of the transducer at a time when each frozen image was derived, the spatial position of the transducer being relative to a stationary coordinate system associated with the object being scanned; and means for displaying said selected ones of said images as a set in an augmented reality setting utilizing said tracking information for said transducer and for said operator's viewpoint such that the set of images is displayed in a spatial configuration where each selected image is spatially arranged according to the spatial position in which the selected image was frozen relative to the stationary coordinate system associated with the object;

means for selectively freezing and adding to said set a further one of said images; and means for selectively removing an image from said set.

11. Apparatus for augmented reality visualization as recited in claim 10, including means for performing said steps of selectively freezing and selectively removing under operator control.

12. Apparatus for augmented reality visualization as recited in claim 10, including means for selectively removing upon a predetermined number of images in said set being reached.

13. A method for augmented reality visualization of ultrasound images, comprising:

deriving ultrasound images of an object maintained in a stationary position;

freezing selected ones of said image;

storing the frozen selected ones of said images and a spatial position of a transducer at a time corresponding to when each frozen image was derived, the spatial position of the transducer being relative to a stationary coordinate system associated with the object being scanned;

displaying said selected ones of said images as a set in a spatial configuration where each selected image is spatially arranged according to the spatial position in which the selected image was frozen relative to the stationary coordinate system associated with the object;

selectively freezing and adding to said set to a further one of said images; and selectively removing an image from said set.

14. A method for augmented reality visualization of ultrasound images, comprising the steps of:

deriving tracking information for a transducer utilized for deriving said ultrasound images;

deriving and storing tracking information for video generated from an operator's viewpoint;

deriving ultrasound images of an object maintained in a stationary position;

freezing selected ones of said images;

storing the frozen selected ones of said images and tracking information for the transducer corresponding to a spatial position of the transducer at a time when each frozen image was derived, the spatial position of the transducer being relative to a stationary coordinate system associated with the object being scanned; and displaying said selected ones of said images as a set in an augmented reality setting utilizing said tracking information for said transducer and for said operator's viewpoint such that the set of images is displayed in a spatial configuration where each selected image is spatially arranged according to the spatial position in which the selected image was frozen relative to the stationary coordinate system associated with the object; and selectively freezing and adding to said set a further one of said images; and selectively removing an image from said set.

15. A method for augmented reality visualization as recited in claim 14, wherein said steps of selectively freezing and selectively removing are performed by said operator.

16. A method for augmented reality visualization as recited in claim 14, wherein said step of selectively removing is automatically performed upon a predetermined number of images in said set being reached.

* * * * *